US005723632A

United States Patent [19]

McMorris

[11] Patent Number: 5,723,632
[45] Date of Patent: Mar. 3, 1998

[54] TOTAL SYNTHESIS OF ANTITUMOR ACYLFULVENES

[75] Inventor: Trevor C. McMorris, LaJolla, Calif.

[73] Assignees: MGI Pharma, Inc., Minnetonka, Minn.; Regents of the University of California, Oakland, Calif.

[21] Appl. No.: 689,461

[22] Filed: Aug. 8, 1996

[51] Int. Cl.$^6$ ........................................ C07D 307/94
[52] U.S. Cl. .................... 549/331; 549/330; 568/347; 568/361; 568/819
[58] Field of Search ................ 549/331, 330; 568/347, 361, 819

[56] References Cited

U.S. PATENT DOCUMENTS

| 5,387,578 | 2/1995 | Angelucci et al. | 514/21 |
| 5,439,936 | 8/1995 | Kelner et al. | 514/546 |

FOREIGN PATENT DOCUMENTS

| 62-234040 | 10/1987 | Japan | C07C 49/737 |
| 91/04754 | 4/1991 | WIPO | A61K 47/48 |

OTHER PUBLICATIONS

Anchel, M., et al., "Antibiotic Substances from Basidiomycetes. VII. Clitocybe Illudens", *Proc. Natl. Acad. Sci. USA*, 36 (5), 300–305, (1950).

Anchel, M., et al., "The Biogenesis of Illudins S and M in Clitocybe Illudens", *Phytochemistry*, 9, 2339–2343, (1970).

Brandsteterova, E., et al., "HPLC Analysis of Novel Anti-Cancer Agents–Illudins and Their Analogs", *J. Liquid Chromatography*, 16 (1), 115–125, (1993).

Brandsteterova, E., et al., "HPLC Determination of a New Anticancer Agent (Acylfulvene) in Serum", *Neoplasma*, 39 (6), 369–373, (1992).

Burres, N.S., et al., "Antitumor Activity and Mechansim of Action of the Novel Marine Natural Products Mycalamide-A and -B and Onnamide", *Cancer Research*, 49, 2935–2940, (Jun., 1989).

Dillman, R.O., et al., "Athymic Mouse Model of a Human T–Cell Tumor", *Cancer Research*, 45, 5632–5636, (Nov., 1985).

French, A.L., et al., "Poisoning with the North American Jack O' Lantern Mushroom", *Clinical Toxicology*, 26 (1&2), 81–88, (1988).

Giovanella, B.C., et al., "Correlation Between Response to Chemotherapy of Human Tumors in Patients and in Nude Mice", *Cancer*, 52, 1146–1152, (1983).

Giovanella, B.C., et al., "DNA Topoisomerase I–Targeted Chemotherapy of Human Colon Cancer in Xenografts", *Science*, 246, 1046–1048, (Nov., 1989).

Goldin, A., et al., "Current Results of the Screening Program at the Division of Cancer treatment, National Cancer Institute", *Europ. J. Cancer*, 17, 129–142, (1981).

Goldin, A., et al., "Historical Development and Current Strategy of the National Cancer Institute Drug Development Program", *In: Methods in Cancer Research, vol. XVI*, Academic Press, Inc., 165–245, (1979).

Hanson, J.R., et al., "Studies in Terpenoid Biosythesis, Part XV. Biosynthesis of the Sesquiterpenoid Illudin M", *J.C.S. Perkins I*, 876–880, 1976.

Hara, M., et al., "6–Deoxyilludin M, a New Antitumor Antibiotic: Fermentation, Isolation and Structural identification", *The Journal of Antibiotics*, 40, 1643–1646, (Nov., 1987).

Harttig, U., et al., "Leaianafulvene, a Sesquiterpenoid Fulvene Derivative from Culture of Mycena Leaiana", *Phytochemistry*, 29 (12), 3942–3944, (1990).

Hirono, I., et al., "Repreoduction of Acute Bracken Poisoning in a Calf with Ptaquiloside, a Bracken Constituent", *The Veterinary record*, 115, Abstract No. 85067284, STN File Server, File Medline, 375–378, (Oct., 1984).

Inoue, K., et al., "Antitumor Efficacy of Seventeen Anticancer Drugs in Human Breast Cancer Xenograft (MX–1) Transplanted in Nude Mice", *Cancer Chemother. Pharamacol.*, 10, 182–186, (1983).

Kawato, Y., et al., "Antitumor Activity of a Camptothecin Derivative, CPT–11, Against Human Tumor Xenografts in Nude Mice", *Cancer Chemother. Pharmacol.*, 28, 192–198, (1991).

Kelner, M.J., et al., "In Vitro and In Vivo Studies on the Anticancer Activity of Dehydroilludin M", *Anticancer Research*, 15, 873–878, (1995).

Kelner, M.J., et al., "Nonresponsiveness of the Metastatic Human Lung Carcinoma MV522 Xenograft to Conventional Anticancer Agents", *Anticancer Research*, 15, 867–872, (1995).

Kelner, M.J., et al., "Preclinical Evaluation of Illudins as Anticancer Agents", *Cancer Research*, 47, 3186–3189, (1987).

Kelner, M.J., et al., "Preclinical Evaluation of Illudness as Anticancer Agents: Basis for Selective Cytotoxicity", *J. Natl. Cancer. Inst.*, 82 (19), 1562–1565, (1987).

Matsumoto, T., et al., "An Alternative of Illudin M", *Tetrahedron Letters*, 14, 1171–1174, (1970).

Matsumoto, T., et al., "Synthesis of Illudin S", *Tetrahedron Letters*, 23, 2049–2052, (1971).

McMorris, T.C., et al., "(Hydroxymethyl) Acyfulvene: An Illudin Derivative with Superior Antitumor Properties", *J. Nat. Prod.*, 59, 896–899, (1996).

McMorris, T.C., et al., "Acyfulvenes, a New Class of Potent Antitumor Agents", *Experientia*, 52, 75–80, (1996).

(List continued on next page.)

Primary Examiner—Nicky Chan
Attorney, Agent, or Firm—Schwegman, Lundberg, Woessner, & Kluth, P.A.

[57] ABSTRACT

The present invention provides a method of synthesizing compounds of formula (I):

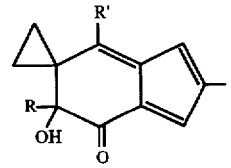

wherein R and R' are independently $(C_1-C_4)$alkyl.

10 Claims, 3 Drawing Sheets

OTHER PUBLICATIONS

McMorris, T.C., et al., "Fungal Metabolites. The Structures of the Novel Sesquiterpenoids Illudin –S and –M", *J. of Amer. Chem. Soc.*, 87 (7), 1594–1600, (1965).

McMorris, T.C., et al., "On the Mechanism of Toxicity of Illudins: The Role of Gluthathione", *Chem. Res. Toxicol.*, 3, 574–579, (1990).

McMorris, T.C., et al., "Structure–Activity Relationships of Illudens: Analogs with Improved Therapeutic Index", *J. Org. Chem.*, 57, 6876–6883, (1992).

McMorris, T.C., et al., "Structure and Reactivity of Illudins", *Tetrahedron*, 45 (17), 5433–5440, (1989).

Schabel, F.M., et al., "Testing Therapeutic Hypotheses in Mice and Man:Observations on the Therapeutic Activity Against Advanced Solid Tumors of Mice Treated with Anticancer Drugs that Have Demonstrated or Potential Clinical Utility for Treatment of Advanced Solid Tumors of Man", In: *Methods in Cancer Research, vol. XVII*, Academic Press, Inc., pp. 3–50, (1979).

Shimomura, O., "The Role of Superoxide Dismutase in Regulating the Light Emission of Luminescent Fungi", *J. of Experimental Botany*, 43, 1519–1525, (1992).

Steel, G.G., et al., "The Response to Chemotherapy of a Variety of Human Tumor Xenografts", *Br. J. Cancer*, 47, 001–013, (1983).

Tanaka, K., et al., "Metabolism by Rat Liver Cytosol of Illudin S, a Toxic Substance of Lampteromyces Japonicus. II. Characterization of Illudin S–Metabolizing Enzyme", *Xenobiotica*, 22 (1), 33–39, (1992).

Tanaka, K., et al., "Metabolism of Illusin S, a Toxic Principle of Lampteromyces Japonicus, by Rat Liver. I. Isolation and Identification of Cyclopropane Ring–Cleavage Metabolites", *Xenobiotica*, 20 (7), 671–681, (1990).

Varki, N.M., et al., "Cloned Low Metastic Variants from Human Lung Carcinoma Metastases", *Anticancer Research*, 10, 637–644, (1990).

Vendetti, J.M., et al., "Current NCI Preclinical Antitumor Screening in Vivo: Results of Tumor Panel Screening, 1976–1982, and Future Directions", *Advances in Pharmacology and Chemotherapy*, 20, 1–20, (1984).

Venditti, J.M., "The National Cancer Institute Antitumor Drug Discovery Program. Current and Future Perspectives: A Commentary", *Cancer Treatment Reports*, 67, 767–772, (Sep., 1983).

Walser, J., et al., "Mode of Action of Illudin S", *Antimicrob. Ag. Chemother.*, 3 (3), 357–362, (1973).

Weinreb, S.M., "Fulvenes Derived from Illudin S", *Tetrahedron Ltrs.*, 38, 3489–3491, (1971).

SCHEME I

TOTAL SYNTHESIS OF ANTITUMOR ACYLFULVENES

BACKGROUND OF THE INVENTION

Natural products from plants and microorganisms have proven to be a major source of active anticancer agents and lead compounds for cancer chemotherapy. Mushrooms of the class Basidiomycetes are an exception. Although they occur widely and some are well known to contain a variety of highly poisonous substances, only *Omphalotus illudens* (jack o'lantern mushroom) is known to produce promising anticancer compounds. These are the sesquiterpenes illudin S and illudin M. The illudins are extremely cytotoxic compounds but have a low therapeutic index particularly in solid tumor systems. However, modification of their structures has yielded several analogs, which possess a greatly improved therapeutic index. Remarkable efficacy has been observed in tests on mouse xenografts of leukemias and various solid tumors.

First and second generation analogs, for example, dehydroilludin M and acylfulvene, have been described (WO 91/04754). A promising compound is a third generation analog hydroxymethylacylfulvene (HMAF). In tests with MV 522 metasiatic lung carcinoma xenografts in nude mice, complete tumor regression was observed in all animals. HMAF also exhibited outstanding activity against breast (MX-1), colon (HT-29) and skin cancers.

The structures of illudin S and illudin M were first published in 1963 (McMorris et al., *J. Am. Chem. Soc.* 85:831 (1963)). Until recently only one total synthesis of these compounds had been reported (Matsumoto et al., *Tetrahedron Lett.* 1171 (1970)). This synthesis involved Michael addition of a cycylopropane intermediate to an appropriately substituted cyclopentenone. The resulting product was then transformed into an intermediate which could undergo aldol condensation to form illudin's six-membered ring. A number of further reactions were required to complete the synthesis.

Padwa et al., (*J. Am. Chem. Soc.* 116:2667 (1994)), have published a synthetic approach to the illudin skeleton using a dipolar cycloaddition reaction of a cyclic carbonyl ylide dipole with cyclopentenone to construct the six-membered ring. Kinder and Bair (*J. Org. Chem.* 59:6955 (1994)), have also employed the Padwa methodology to synthesize illudin M. However, these syntheses are long and not well suited for making acylfulvenes on a large scale. Thus, a continuing need exists for improved methods for synthesizing acylfulvenes.

SUMMARY OF THE INVENTION

The present invention provides a method of synthesizing compounds of formula (I):

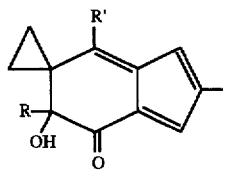

wherein R and R' are independently $(C_1-C_4)$alkyl, preferably methyl. According to the invention, a method is provided of synthesizing a compound of formula (V), a preferred intermediate in the synthesis of compounds of formula (I),:

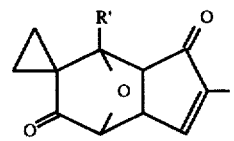

comprising the steps of coupling a cyclopentanone of formula (II):

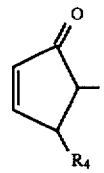

wherein $R_4$ is $—O—C(R_9)_2O(R_9)$, wherein $R_9$ is $(C_1-C_4)$ alkyl, preferably methyl;

with a cyclic carbonyl ylide dipole of formula (III):

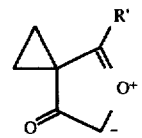

to form a compound of formula (IV):

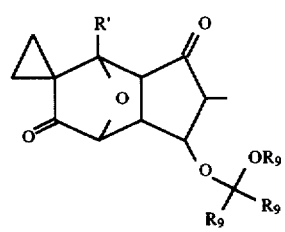

and treating compound (IV) with base to form a ketone of formula (V).

The present method further may further comprise the steps of dihydroxylating the ketone to yield a compound of formula (VI):

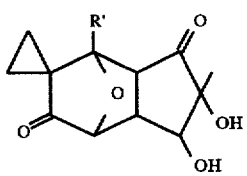

and treating the compound of formula (VI) with a removable 1,2-diol protecting reagent to yield an intermediate of formula (VII):

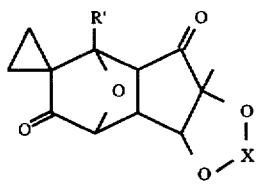

wherein X is a removable 1,2-diol protecting group. Protecting groups may be introduced by forming a cyclic acetal by treatment with an aldehyde or ketone such as acetone, formaldehyde, acetaldehyde or benzaldehyde. For example, an isopropylidene derivative (acetonide) may be introduced by reaction with acetone. Preferably, the isopropylidene group is introduced by acid-catalyzed exchange with 2,2-dimethoxypropane.

The method further comprises the steps of treating compound (VII) with RMgCl, where R is $(C_1-C_4)$alkyl, to yield a Grignard product of formula VIII:

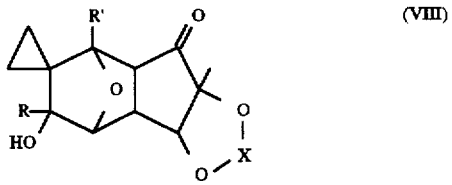

(VIII)

and cleaving the oxybridge to yield a diol of formula (IX):

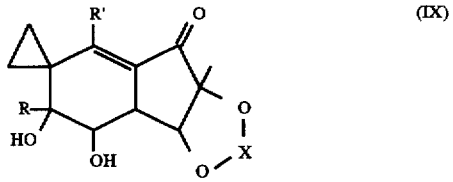

(IX)

The method further comprises the step of removing the diol protecting group to yield a tetraol of formula (X):

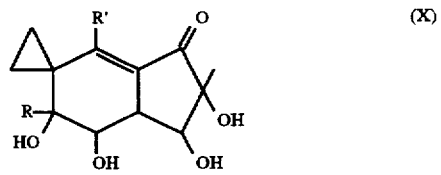

(X)

The tetraol is then converted to an orthoester of formula (XI):

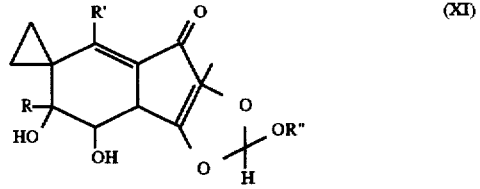

(XI)

wherein R" is $(C_1-C_3)$alkyl; and the cis hydroxyls are eliminated to yield a dienone of formula (XII):

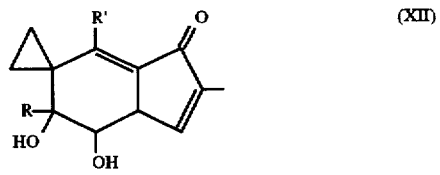

(XII)

The method further comprises the steps of reducing the compound of formula (XII) to convert the ketone to an alcohol, under conditions which dehydrate the resulting alcohol to yield a fulvene of formula (XIII):

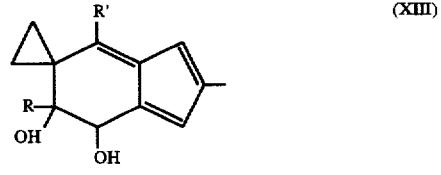

(XIII)

The fulvene of formula (XIII) is then oxidized to yield a compound of formula (I):

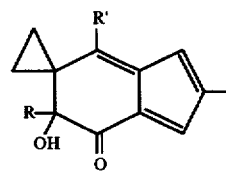

(I)

The present invention also provides a method of synthesizing a compound of formula (XVII):

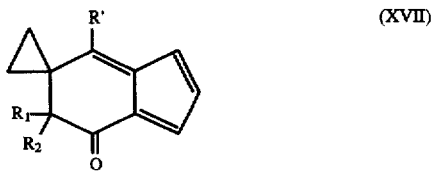

(XVII)

wherein $R_1$ is OH, $R_2$ is H, and R' is $(C_1-C_4)$alkyl, preferably methyl.

According to the present invention, a method is provided of synthesizing a diketone of formula (XIII), a preferred intermediate in the synthesis of compounds of formula (XVII),:

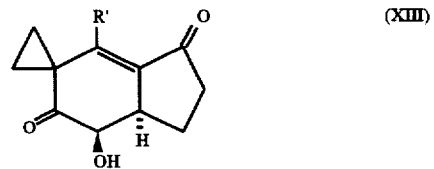

(XIII)

comprising the steps of
(a) cleaving the oxybridge in the compound of formula (XIV):

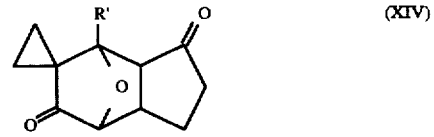

(XIV)

to yield a diketone of formula (XIII).

The method further comprises the steps of
(b) protecting the hydroxyl group in the compound of formula (XIII) with a removable hydroxyl protecting group X; and
(c) introducing a double bond in the five-membered ring to yield a compound of the formula (XV):

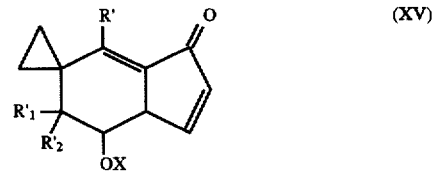

(XV)

wherein $R'_1$ and $R'_2$ together are keto; and
X is a removable hydroxyl protecting group. Removable hydroxyl protecting groups may be introduced by reaction with a suitable reagent, such as a reagent of the formula $((C_1-C_4)\text{alkyl})_3\text{SiCl}$, including triethylsilyl (TES) chloride, trimethylsilyl (TMS) chloride, t-butyldimethylsilyl (TBDMS) chloride, dimethyl (1,2,2-trimethylpropyl)silyl chloride, or tris(isopropyl)silyl; and methoxymethyl chloride, β-methoxyethoxymethyl chloride, and isobutylene.

The method further comprises the steps of
(d) reducing both keto groups to yield hydroxy groups under conditions that yield a compound of formula (XVI):

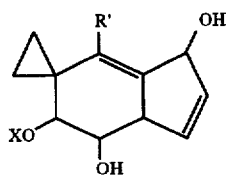
(XVI)

(e) eliminating the cyclopentenol hydroxyl group; and
(f) oxidizing the cyclohexanol hydroxyl group and removing hydroxyl protecting group X to yield a compound of formula (XVII):

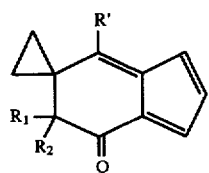
(XVII)

wherein $R_1$ is OH and $R_2$ is H.
The method additionally comprises the step of
(g) following step (d), treating the alcohol with mesyl chloride in the presence of a base to produce a mesylate of the formula (XVIII):

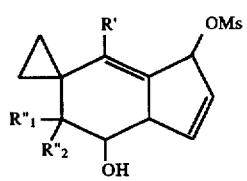
(XVIII)

wherein $R''_1$ x is —OX, $R''_2$ is absent and R is H.
The present invention further provides a method of synthesizing compounds of the formula (XXIII):

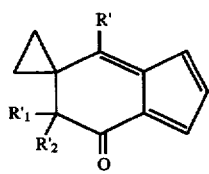
(XXIII)

wherein $R'_1$ and $R'_2$ together are ethylenedioxy, and R' is $(C_1-C_4)$alkyl, preferably methyl.

According to the present method, the carbonyl group of the compound of formula (XIII) is converted to an acetal group to yield a compound of formula (XIX):

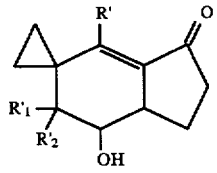
(XIX)

The method further comprises the steps of
(b) protecting the hydroxyl group in the compound of formula (XIX) with a removable hydroxyl protecting group X; and
(c) introducing a double bond in the five-membered ring to yield a compound of the formula (XX):

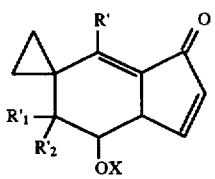
(XX)

wherein X is a removable hydroxyl protecting group.
The method further comprises the steps of
(d) reducing the keto group to yield a hydroxy group under conditions that yield a compound of formula (XXI):

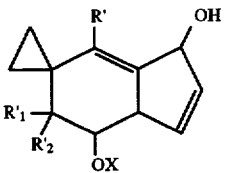
(XXI)

(e) eliminating the cyclopentenol hydroxyl group;
(f) removing hydroxyl protecting group X to yield a compound of formula (XXII):

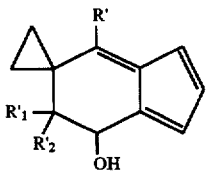
(XXII)

and
(g) oxidizing the cyclohexanol hydroxyl group to yield a compound of formula (XXIII):

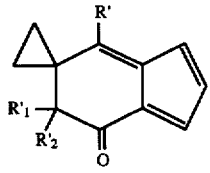
(XXIII)

The method further comprises the step of
(h) following step (d), treating the alcohol with mesyl chloride to produce a mesylate of the formula (XXIV):

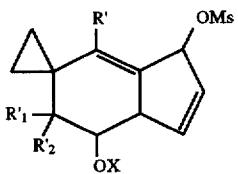
(XXIV)

With respect to both mesylates of formulas (XVIII) and (XXIV), the mesylates are relatively unstable and convert to fulvenes upon standing. Removal of the protecting group X and oxidation yield compounds of formulas (XVII) and (XXIII), respectively.

The invention also provides novel compounds of formula I-XXIV, all of which are useful as intermediates in the synthesis of 6-substituted acylfulvene analogs (6-substituted acylfulvenes) as disclosed, for example, in Kelner et al., U.S. Pat. No. 5,523490, or which have antitumor or cytotoxic activity per se.

DETAILED DESCRIPTION OF THE INVENTION

Figure 1:
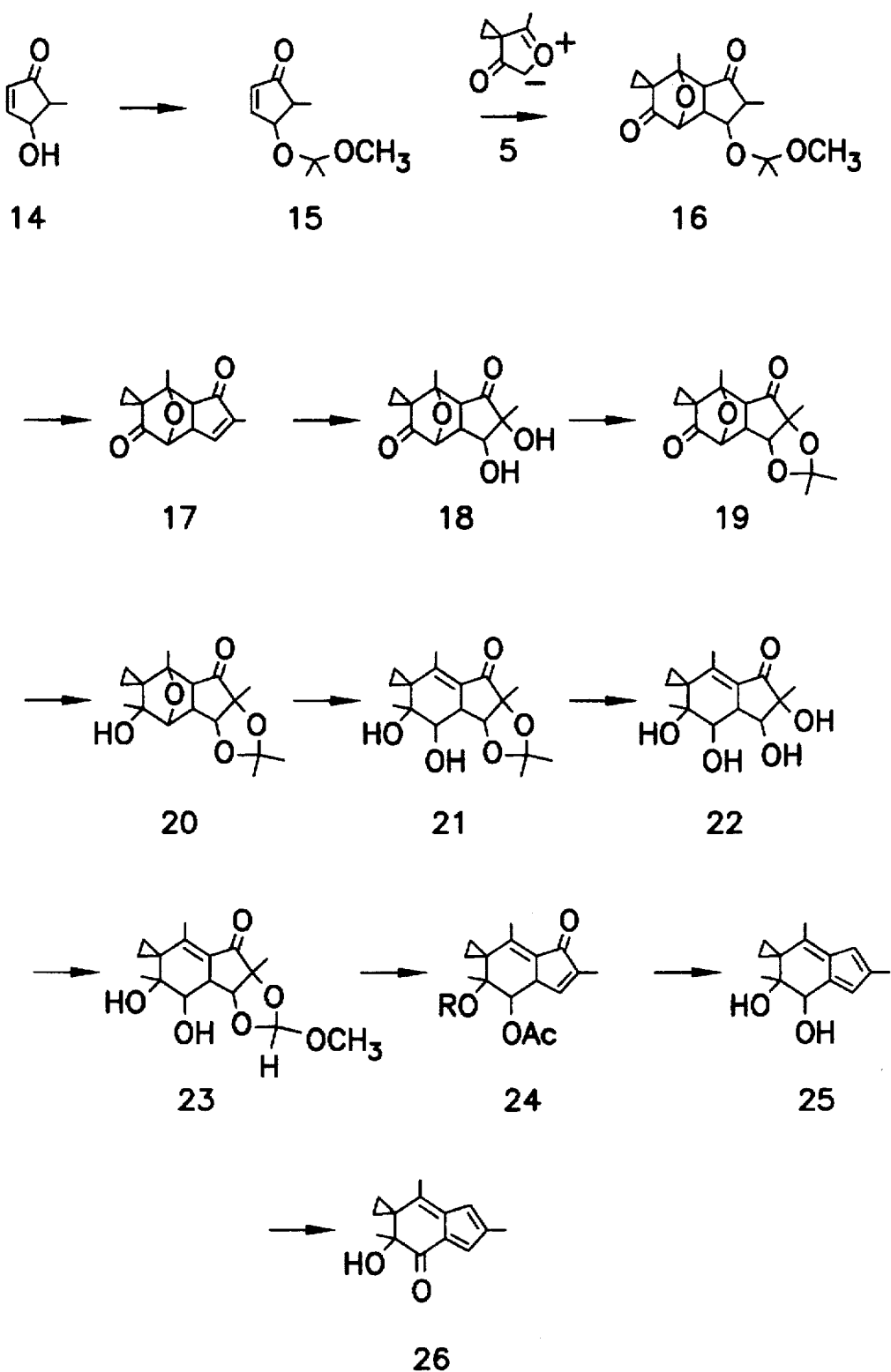
FIG. 1 is a schematic representation of the synthesis of a compound of Formula (I), specifically compound 26.

An illudin analog of formula (I), where R and R' are methyl (compound 26), can be synthesized by utilizing FIG. 1. The numbers following the named compounds refer to the numbered compounds of Schemes I, II and III. The starting compound (14) is readily prepared from furfural and methylmagnesium chloride followed by acid catalyzed rearrangement (Piancatelli et al., Tetrahedron Lett. 3555 (1976)). Protection of the hydroxyl in 14 by forming the acetal derivative 15, for example, followed by reaction with ylide 5 gives the adduct 16 (84% yield). Mild base treatment (KOH-MeOH, room temp., 1 h) of 16 affords the unsaturated ketone 17 (95%). Dihydroxylation of 17 with $OSO_4$, NMO in THF (room temp., 24 h) gives the cis-dihydroxy product 18 which is converted to the acetonide 19 with dimethoxy propane and p-TsOH (87% for the two steps). Regioselective reaction of 19 with methylmagnesium chloride (in THF, -78° C.) affords the Grignard product 20. Treatment of 20 with 10% KOH-MeOH at 80° C. for 2 h cleaves the oxybridge giving the diol 21 (75% for the two steps). The structure (21) has been confirmed by X-ray crystallographic analysis which indicates trans relationship of the two hydroxyls.

Hydrolysis of the acetonide with Dowex resin ($H^+$ form) in MeOH at room temperature for 12 h affords the tetraol 22 in 95% yield. Conversion of 22 to the orthoester 23 by treatment with trimethylorthoformate and p-TsOH at room temperature followed by heating 23 at 190° C. under reduced pressure results in elimination of the cis hydroxyls yielding the dienone. The yields in this reaction are rather low but can be improved by adding acetic anhydride. A good yield of the monoacetate and diacetate (24 a, b) is obtained. Reduction of the ketone with $NaBH_4$-$CeCl_3$ gives the corresponding alcohol which is unstable and is converted to the fulvene on standing. The acetate groups are removed by treatment with lithium aluminum hydride and the resulting fulvene 25 is oxidized with the Dess-Martin reagent to±acylfulvene 26. The overall yield for the last four steps is approximately 30%.

Figure 2:
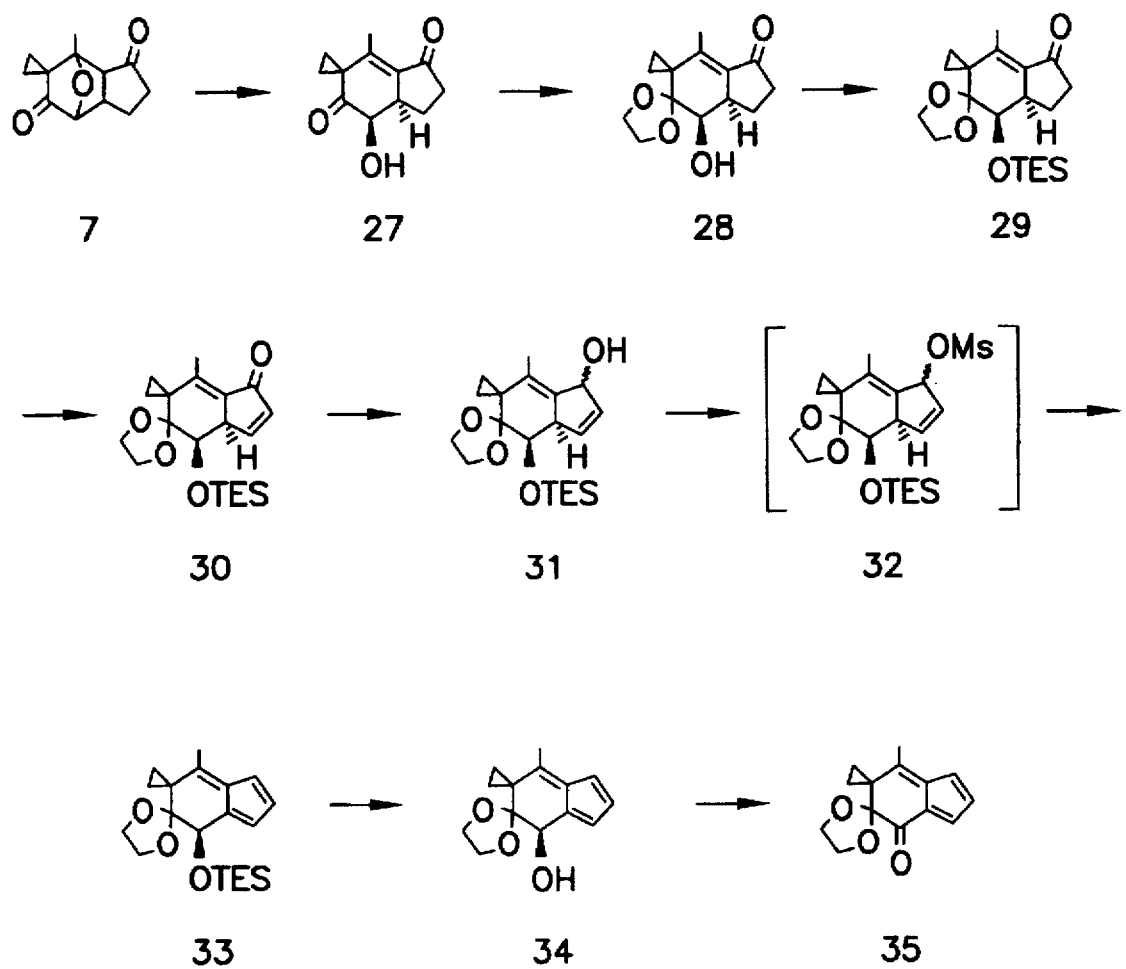
FIG. 2 is a schematic representation of the synthesis of compound of Formula (XV), specifically compound 35.

An acylfulvene analog of formula (XV) where $R'_1$ and $R'_2$ together are ethylenedioxy (compound 35), may be synthesized as shown in FIG. 2. The oxybridge in the intermediate 7 is cleaved with $K_2CO_3$ in isopropanol at room temperature giving the diketone 27 (82%). Regioselective acetal formation (ethylene glycol, p-TsOH, $C_6H_6$, room temperature) gives in quantitative yield the monoacetal 28. Protection of the hydroxyl as the triethyl silyl ether (triethylsilylchloride, pyridine, 60° C.) is quantitative. A double bond is introduced into compound 29, by treatment with benzene seleninic anhydride in chlorobenzene at 95° C., yielding cross conjugated ketone 30 (78%). Reduction of 30 ($NaBH_4$, $CeCl_3$, 7 $H_2O$ in MeOH) gives alcohol 31. This compound on treatment with methane sulfonyl chloride and triethylamine gives the fulvene 33 (via the unstable mesylate 32). Removal of the silyl protecting group (p-TsOH, acetone-water 1:1) gives the alcohol 34, which upon oxidation with pyridinium dichromate in dichloromethane affords the acylfulvene 35 (60% yield for four steps).

Figure 3:
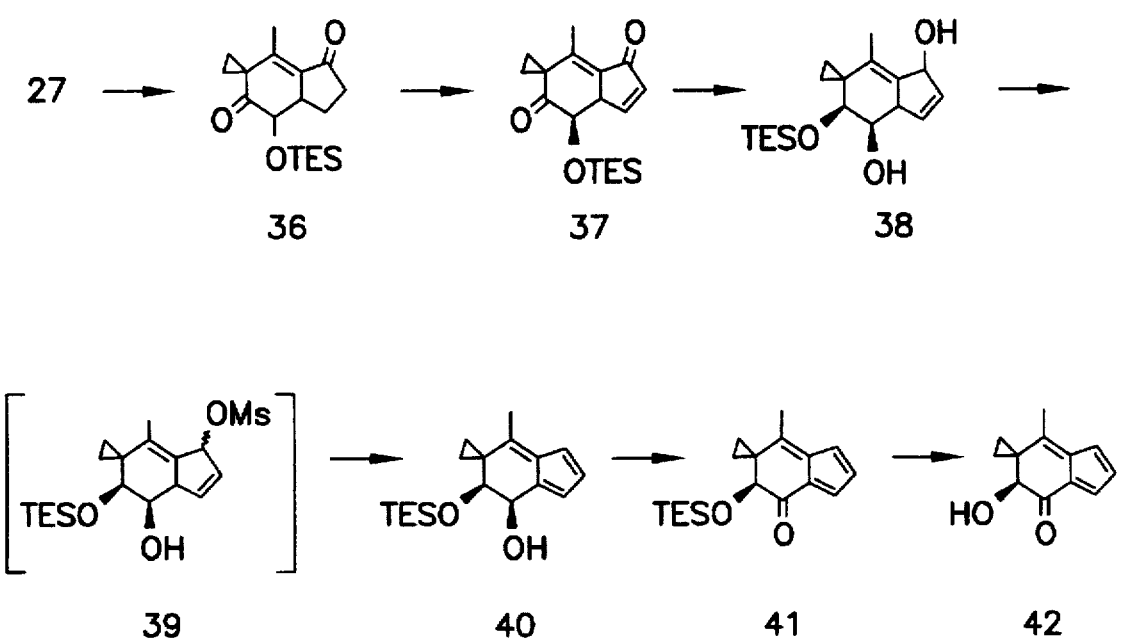
FIG. 3 is a schematic representation of the synthesis of compound of Formula (XV), specifically compound 42.

Another analog of formula (XVII) where $R_1$ is OH and $R_2$ is H (compound 42) can be made from intermediate 27. As shown in FIG. 3, compound 27 is converted to the triethylsilyl (TES) ether 36. A double bond is then introduced in the five membered ring by reaction with phenylseleninic anhydride giving 37 in good yield. Reduction of the diketone with sodium borohydride-ceric chloride gives the corresponding alcohols accompanied by rearrangement of the TES group, resulting in compound 38. Treatment of the latter with triethylamine and mesylchloride gives the unstable mesylate 39 which directly yields the fulvene 40. Oxidation of 40 with Dess-Martin reagent and removal of the silyl protecting group gives±acylfulvene analog 42.

The compounds of formulas (I), (XVII) and ((XXIII) and interradiates thereof are useful as antineoplastic agents, i.e., to inhibit tumor cell growth in vitro or in vivo, in mammalian hosts, such as humans or domestic animals, and are particularly effective against solid tumors and multi-drug resistant tumors. These compounds may be particularly useful for the treatment of solid tumors for which relatively few treatments are available. Such tumors include epidermoid and myeloid tumors, acute (AML) or chronic (CML), as well as lung, ovarian, breast and colon carcinoma. The compounds can also be used against endometrial tumors, bladder cancer, pancreatic cancer, lymphoma, Hodgkin's disease, prostate cancer, sarcomas and restitular cancer as well as against ramors of the central nervous system, such as brain tumors, neuroblastomas and hematopoietic cell cancers such as B-cell leukemia/lymphomas, myelomas, T-cell leukemia/lymphomas, and small cell leukemia/lymphomas. These leukemia/lymphomas could be either acute (ALL) or chronic (CLL).

The compounds may also be incorporated in a pharmaceutical composition, such as pharmaceutical unit dosage form, comprising an effective anti-neoplastic amount of one or more of the illudin analogs in combination with a pharmaceutically acceptable carrier.

The methods of the present invention may also be adapted to make pharmaceutically acceptable salts of compounds of formula (I), (XVII) or (XXIII). Pharmaceutically acceptable salts include, where applicable, salts such as amine acid addition salts and the mono-, di- and triphosphates of free hydroxyl groups. Amine salts include salts of inorganic and organic acids, including hydrochlorides, sulfates, phosphates, titrates, tartarates, malates, maleates, bicarbonates, and the like. Alkali metal amine or ammonium salts can be formed by reacting hydroxyaryl groups with metal hydroxides, amines or ammonium.

The compounds can be formulated as pharmaceutical compositions and administered to a mammalian host, such as a human cancer patient, in a variety of forms adapted to the chosen route of administration, i.e., orally or parenterally, by intravenous, intraperitoneal, intramuscular or subcutaneous routes.

The subject can be any mammal having a susceptible cancer, i.e., a malignant cell population or tumor. The analogs are effective on human tumors in vivo as well as on human tumor cell lines in vitro.

Thus, the compounds may be orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, butcat tablets, troches, capsules, elixirs, suspensions, syrups, wafers, and the like. Such compositions and preparations should contain at least 0.1% of active compound. The percentage of the compositions and preparations may, of course, be varied and may conveniently be between 2 to about 60% of the weight of a given unit dosage form. The amount of active compound ha such therapeutically useful compositions is such that an effective dosage level will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion use can include sterile aqueous solutions or dispersions or sterile powders comprising the active ingredient which are adapted for the extemporaneous preparation of sterile injectable of infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, or example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of compounds made according to the present methods can be determined by correlating the compounds' in vitro activity, and in vivo activity in animal models, such as murine or dog models as taught for illudin analogs such as those of U.S. Pat. Nos. 5,439,936 and 5,523,490, to activity in higher mammals, such as children and adult humans as taught, e.g., in Borch et al. (U.S. Pat. No. 4,938,949).

The therapeutically effective amount of analog necessarily varies with the subject and the tumor to be treated. However, it has been found that relatively high doses of the analogs can be administered due to the decreased toxicity compared to illudin S and M. A therapeutic amount between 30 to 112,000 µg per kg of body weight is especially effective for intravenous administration while 300 to 112,000 µg per kg of body weight is effective if administered intraperitoneally. As one skilled in the art would recognize, the amount can be varied depending on the method of administration.

The invention will be further described by reference to the following detailed examples.

EXAMPLES

Example I—Synthesis of Compound 36

General

Solvents were dried and distilled prior to use. THF and diethyl ether were distilled from sodium-benzophenone, $CH_2Cl_2$ and triethylamine from $CaH_2$. Melting points are uncorrected. 1H- and 13C-NMR spectra were measured at 300 MHz and 75 MHz, respectively. High resolution mass spectra were determined at 70 ev (EI) by the Mass Spectrometry Service Laboratory at the University of Minnesota. Column chromatography was performed on silica gel (Davisil 230–425 mesh, Fisher Scientific ). In some cases, a small amount of triethylamine was used to neutralize the silica gel.

Compound 15

To a solution of 14 (0.448 g, 4 mmol) in 2-methoxypropene (1.55 ml, 16.2 mmol), a drop of $POCl_3$ was added under Ar. The solution was stirred at 25° C. for 12 hours and quenched by 3 drops of $Et_3N$. The volatile components were removed in vacuo and the product 15 was obtained as a brown liquid which crystallized below 0° C. (0.69 g, 94.3%). $^1H$ NMR($CDCl_3$): δ7.43(dd, 1H), 6.17(d, 1H), 4.58(br s, 1H), 3.26(s, 3H), 2.26(m, 1H), 1.41(s, 3H), 1.40(s, 3H), 1.22(d, 3H).

Compound 16

To a mixture of 15 (5.02 g, 27.3 mmol), rhodium acetate (145 mg, 0.33 mmol), DMF(500 uL) in $CH_2Cl_2$(50 mL), a solution of 4 (6.0 g, 39.5 mmol) in $CH_2Cl_2$ (50 mL) was added dropwise within 10 minutes at 40° C. The orange-red solution was refluxed at 40° C. for 1.5 hours and the solvent was removed in vacuo. Chromatography (Hexane/EtOAc, 10:2) gave product 16 as white crystals (7.10 g, 84.5%). m.p.: 142°–144° C.; $^1H$ NMR ($CDCl_3$): δ4.98(s, 1H), 4.13 (dd, 1H), 3.28(s, 3H), 2.82(t, 1H), 2.63(d, 1H), 2.54(m, 1H), 1.43(s,3H), 1.42(s,3H), 1.18(s, 3H), 1.08(d, 3H), 1.29(m, 1H), 1.03–1.16(m, 2H), 0.72(m, 1H); $^{13}C$ NMR ($CDCl_3$): δ213.3, 212.1, 101.2, 87.4, 81.8, 73.8, 59.4, 50.4, 49.7, 45.8, 39.0, 26.0, 25.1, 14.1, 13.7, 12.4, 11.4. IR (film, $cm^{-1}$): 2985, 1738, 1389, 1339, 1173, 1080, 1052, 991, 859, 827; HRMS calcd. for $C_{17}H_{24}O_5$: 308.1624, found: 308.1625

Compound 17

The solution of 16 (594.3 mg, 1.93 mmol) in 5% KOH-MeOH (35 ml) was stirred at room temperature for 1 hour. The generated red solution was then neutralized and extracted with EtOAc. The combined organic phase was washed with sat. brine (20 ml×2) and dried over $Na_2SO_4$. Chromatography (Hexanes/EtOAc, 10:3)gave the product 17 as white crystals (390.9 mg, 93%).m.p.: 108.5°–109.4° C.; $^1H$ NMR ($CDCl_3$): δ7.15(d, 1H), 4.24(s, 1H), 3.21(br s, 1H), 2.55(d, 1H), 1.75(s, 3H), 1.23(s, 3H), 1.25(m, 1H), 1.10( m, 1H), 0.97(m, 1H), 0.74(m, 1H); $^{13}C$ NMR ($CDCl_3$): δ211.77, 205.86, 154.23, 145.86, 86.05, 80.93, 54.68, 45.82, 37.56, 14.05, 13.22, 11.58, 10.22; IR (film, $cm^{-1}$): 1754, 1703, 1639, 1389, 1339, 997; HRMS calcd. for $C_{13}H_{14}O_3$: 218.0943, found: 218.0941

Compound 19

To a solution of 17 (349.4 mg, 1.60 mmol), NMO (355 mg) in THF (17.7 ml) and $H_2O$ (0.5 ml), was added $OsO_4$-THF solution (2.5 wt %, 3.5 ml). After stirred at 25° C. for 21 hrs, the reaction was quenched by aqueous $Na_2SO_3$ solution. The reaction mixture was extracted with EtOAc. The organic phase was washed with sat. NaCl solution, dried over $Na_2SO_4$ and concentrated. The crude diol product 18 was used for next step without further purification. A small amount of 18 was purified by chromatography. $^1H$ NMR ($CDCl_3$): δ4.60(s, 1H), 3.95(t, 1H), 3.01(d, 1H), 2.94(d, 1H), 2.88(s, 1H), 2.81(dd, 1H), 1.36(s, 3H), 1.28(s, 3H), 1.33(m, 1H), 1.18(m, 1H), 1.06(m, 1H), 0.75(m, 1H)

The crude diol 18 was reacted with 2,2-dimethoxypropane (0.8 ml, 4 eq.) in $CH_3CN$ (8.0 ml) in the presence of a trace of pTsOH. After being stirred at 25° C. for 10 hrs, the mixture was diluted with $CH_2Cl_2$ and washed with sat. $NaHCO_3$ solution and brine. Chromatography (Hexanes/EtOAc, 10:2) gave the product 19 as white crystals (308.5 mg, 87.3%). m.p.: 178.5°–179.5° C.; $^1H$ NMR ($CDCl_3$): δ4.58(s, 1H), 4.36(s, 1H), 2.89(q, 2H), 1.42(s, 3H), 1.34(s, 3H), 1.31(s, 3H), 1.20(s, 3H), 1.28(m, 1H), 1.16(m, 1H), 1.05(m, 1H), 0.69–0.76(m, 1H); $^{13}C$ NMR ($CDCl_3$): δ215.53, 210.05, 110.66, 87.96, 86.44, 85.03, 83.34, 57.36, 45.37, 38.49, 27.17, 25.96, 16.92, 14, 19, 13.57, 12.32; IR (film, $cm^{-1}$): 2986, 1746, 1372, 1338, 1247, 1216, 1158, 1082; HRMS calcd. for $C_{16}H_{20}O_5$: 292.1311, found: 292.1315

Compound 21

To the solution of 19 (289.5 mg, 0.99 mmol) in THF (25 ml) at −78° C., was added MeMgCl-THF solution (3.0M, 830 μl, 2.5 eq) slowly. After 2.5 hrs, the solution was warmed to 0° C. and quenched with sat. $NH_4Cl$ solution. The solution was extracted with EtOAc and the organic phase was washed with brine solution. Concentration of dried organic solution gave the crude compound 20. $^1H$ NMR ($CDCl_3$): δ4.29(s, 1H), 4.23(s, 1H), 3.45(d, 1H), 2.78(d, 1H), 1.39(s, 3H), 1.35(s, 3H), 1.33(s, 3H), 1.24(s, 3H), 1.01(s, 3H), 0.77(m, 1H), 0.67(m, 1H), 0.52(m, 1H), 0.20(m, 1H); IR (film, $cm^{-1}$): 3492, 2984, 2934, 1743, 1454, 1373, 1257, 1210, 1159, 1082; HRMS calcd. for $C_{17}H_{24}O_5$: 308.1624, found: 308.1629.

The crude compound 20 was dissolved in 10% KOH-MeOH solution. The red mixture was heated at 80° C. for 2 hrs then partitioned between $H_2O$ and $CH_2Cl_2$. The organic layer was washed with brine then dried over $Na_2SO_4$. Chromatography (Hexanes/EtOAc, 10:15) gave the product 21 as white crystals (228.0 mg, 75%) (inseparable mixture of isomers shown by $^1H$ NMR) m.p.:162.0°–164.0° C.; $^1HNMR$ ($CDCl_3$): δ4.52(d, 1H), 3.88(dd, 1H), 3.38(m, 1H), 2.33(d, 1H), 2.18(s, 1H), 1.81(d, 3H), 1.42(s, 3H), 1.38(s, 3H), 1.07(s, 3H), 0.97–1.18(m, 4H); $^{13}C$ NMR ($CDCl_3$): δ201.52, 152.89, 126.44, 112.96, 85.95, 81.34, 73.14, 72.31, 44.44, 29.41, 28.71, 28.22, 22.82, 21.07, 14.11, 12.58, 7.58; IR (film, $cm^{-1}$): 3455, 2987, 2935, 1694, 1599, 1445, 1373, 1240, 1212, 1092, 1048; HRMS calcd. for $C_{17}H_{24}O_5$: 308.1624, found: 308.1624

Compound 22

The compound 21 (60.9 mg, 0.20 mmol) was stirred with Dowex 50w-x16 resin (2.96 g) in MeOH (5.0 ml) at r.t. for 22 hrs. The resin was filtered away and the filtrate was washed with sat. $NaHCO_3$, sat. NaCl and dried over $Na_2SO_4$. Chromatography ($CH_2Cl_2$/MeOH, 10:1) gave the product as white crystals (49.5 mg, 93%). m.p.: 149.0°–151.0° C.; $^1H$ NMR ($CD_3OD$): δ3.83(d, 1H), 3.81(s, 1H), 3.25(m, 1H), 1.90(d, 3H), 1.25(s, 3H), 1.07(s, 3H), 0.99–1.11(m, 4H); $^{13}C$ NMR ($CD_3OD$): δ202.95, 156.24, 127.16, 76.44, 74.38, 74.12, 71.69, 44.52, 30.07, 23.14, 20.03, 14.56, 13.30, 8.20; HRMS calcd. for $C_{14}H_{20}O_5$: 268.1311, found: 268.1312.

Compound 24a and 24b

To the solution of 22 (40.2 mg, 0.15 mmol) and pTsOH (3.0 mg) in THF (3.0 ml), was added $HC(OCH_3)_3$ (130 μl, 8 eq.) at 25° C. After 2 hrs, sat. $NaHCO_3$ solution was added and the mixture was extracted with EtOAc. The combined organic phase was washed with brine and dried over $Na_2SO_4$. Concentration of the filtrate gave the ortho ester 23 (46.3 mg, 100%) as the intermediate for next reaction.

The ortho ester 23 (35.7 mg, 0.12 mmol) in $Ac_2O$ (2.0 ml) was heated at 150° C. for 1 hr. To the cooled reaction solution was added sat. $NaHCO_3$ solution and extracted with EtOAc. The organic phase was washed with brine and dried over $Na_2SO_4$. Chromatography (Hexanes/EtOAc, 10:3 to 10:7) gave the products 24a and 24b as white crystals in 57.3% (18.2 mg) and 9.8% (3.6 mg) respectively.

Product 24a: m.p.: 119°–121° C.; $^1H$ NMR ($CDCl_3$): δ6.98(s, 1H), 5.25(d, 1H), 3.92(br s, 1H), 1.95(s, 3H), 1.92(s, 3H), 1.80(t, 3H), 0.94–1.42(m, 4H); $^{13}C$ NMR ($CDCl_3$): δ195.59, 170.87, 147.53, 145.85, 145.25, 128.16, 74.16, 72.64, 41.02, 30.30, 22.93, 20.89, 13.48, 11.19, 11.00, 7.70; IR (film, $cm^{-1}$): 3431, 2982, 2914, 1735, 1671, 1613, 1437, 1374, 1237, 1222, 1086, 1027; HRMS calcd. for $C_{16}H_{20}O_4$: 276.1362, found: 276.1363.

Product 24b: m.p.: 189.3°–191.2° C.; $^1H$ NMR ($CDCl_3$): δ6.95(s, 1H), 6.12(d, 1H),3.49(br s, 1H), 2.00(s, 3H), 1.97(s, 3H), 1.92(s, 3H), 1.79(s, 3H), 1.30(s, 3H), 0.92–1.27(m, 4H); $^{13}C$ NMR ($CDCl_3$): δ195.35, 170.17, 170.35, 146.76, 146.00, 145.47, 127.95, 83.75, 70.53, 41.12, 29.27, 22.38, 20.78, 17.23, 12.35, 11.39, 10.95, 9.11.

Compound 26 Acylfulvene from 24a

To the clear solution of 24a (2.3 mg, 8.8 umol), $CeCl_3.7H_2O$ (24.9 mg, 8.0 eq) in Methanol (78 ul) and THF (155ul) at 0° C., excess of $NaBH_4$ was added in one portion. After 15 minutes at 0° C., the suspension was stirred at 25° C. for 30 minutes. At 0° C., the mixture was quenched with 5% HCl solution and Sat.NH4Cl solution and extracted with $CH_2Cl_2$. The organic phase was washed with $H_2O$ and dried over $MgSO_4$. Concentration and chromatography (Hexanes/EtOAc, 10:5) gave the product as yellow solid (1.8 mg, 84%). $^1H$ NMR (CDCl3): δ6.06(s, 1H), 6.01(s, 1H), 5.84(s, 1H), 2.21(s, 3H), 2.04(s, 3H), 1.81(s, 3H), 1.15(s, 3H), 0.62–1.44(m, 4H);

The yellow compound was then dissolved in absolute ethanol (100 ul) and a trace of KCN was added. The solution was stirred overnight at 25° C. and TLC showed the compound 25 was the exclusive product. The solution was diluted with ether and washed with sat.brine and dried over $Na_2SO_4$.

After concentration, the crude diol 25 was oxidized by Dess-Martin reagent (11.8 mg) in $CH_2Cl_2$ solution (1.2 ml). After being stirred at 25° C. for 1 hour, the reaction solution was diluted with ether and quenched with the mixture of aqueous sodium bicarbonate and sodium bisulfite. The organic phase was washed with sat. $NaHCO_3$ and sat. NaCl solution and dried over $NaSO_4$. Concentration and chromatography (Hexanes/EtOAc, 10:1) gave product 26 Acylfulvene as a yellow gum (1.1 mg, 47% from 24a). $^1H$ NMR ($CDCl_3$): δ7.16 (s, 1H), 6.43(t, 1H), 2.15(s, 3H), 2.00(s, 3H), 1.38(s, 3H), 0.70–1.55(m, 4H); IR (film, $cm^{-1}$): 3464, 2922, 2851, 1723, 1664, 1610, 1487, 1441, 1355, 1327, 1264, 1095, 1031; HRMS calcd. for $C_{14}H_{16}O_2$: 217.1229($M+H^+$), found: 217.1224($M+H^+$).

Compound 26 Acylfulvene from 24b.

To the clear solution of 24b (4.1 mg, 0.013 mmol), $CeCl_3 \cdot 7H_2O$ (39.5 mg, 0.11 mmol) in Methanol (100 ul) and THF(200 ul) at 0° C., excess of $NaBH_4$ was added in one portion. After 1 hour at 0° C., the suspension was stirred at 25° C. for 15 minutes. At 0° C., the mixture was quenched with 5% HCl solution and Sat.$NH_4Cl$ solution and extracted with $CH_2Cl_2$. The organic phase was washed with $H_2O$ and dried over $MgSO_4$. Concentration and chromatography (Hexanes/EtOAc, 10:3) gave the product as yellow solid (3.9 mg, 100%). $^1HNMR$ ($CDCl_3$): δ6.24(s, 1H), 6.18(s, 1H), 6.02(d, 1H), 2.06(s, 3H), 2.03(s, 3H), 1.89(s, 3H), 1.82(s, 3H), 1.50(s, 3H), 1.39(m, 1H), 0.99–1.07(m, 3H);

The yellow solid (3.0 mg, 0.01 mmol) was redissolved in ether (0.6 ml) and added to the reaction vial with $LiAlH_4$ (12 mg, 0.31 mmol) in ether (0.4 ml) at 0° C. The suspension was stirred at 0° C. for 30 minutes and warmed up to 25° C. for 20 minutes. The reaction was quenched with acetone then 5% HCl solution and sat. $NH_4Cl$ solution were added. The mixture was extracted with ether. The combined ether phase was washed with sat. NaCl solution and dried over $NaSO_4$. Remove of solvent gave the crude diol 25.

The crude diol 25 was oxidized by Dess-Martin reagent (70 mg) in $CH_2Cl_2$ solution (1.5 ml). After being stirred at 25° C. for 1 hour, the reaction solution was diluted with ether and quenched with the mixture of aqueous sodium bicarbonate and sodium bisulfite. The organic phase was washed with sat. $NaCO_3$ and sat. NaCl solution and dried over $NaSO_4$. Concentration and chromatography (Hexanes/EtOAc, 10:1) gave product 26 Aeylfulvene as a yellow gum (0.7 mg, 33% from 24b). $^1H$ NMR ($CDCl_3$): δ7.16(s, 1H), 6.43(t, 1H), 2.15(s, 3H), 2.00(s, 3H), 1.38(s, 3H), 0.70–1.55 (m, 4H); IR (film, $cm^{-1}$): 3464, 2922, 2851, 1723, 1664, 1610, 1487, 1441, 1355, 1327, 1264, 1095, 1031; HRMS calcd. for $C_{14}H_{16}O_2$: 217.1229 ($M+H^+$), found: 217.1224 ($M+H^+$).

Example II—Synthesis of Compound 35

General

Melting points are uncorrected. $^1H$ and $^{13}C$ NMR spectra were measured at 300 and 75 MHz. High resolution mass spectra were determined at the University of Minnesota Mass Spectrometry Sendee Laboratory. All chromatography used silica gel (Davisil 230–425 mesh, Fisher Scientific) and solvent was ethyl acetate and hexanes. Analytical TLC was carried out on Whatman 4420 222 silica gel plates. Reactions were routinely monitored by TLC. Yield was calculated after recycling starting materials.

Compound 7

Compound 7 was made following literature as a white solid: mp 134°–6° C.; IR (KBr) 2993, 2952, 1757, 1743, 1454 $cm^{-1}$; $^1H$ NMR ($CDCl_3$) δ0.74 (m, 1H), 1.03 (m, 1H), 1.13 (m, 1H), 1.25 (s, 3H), 1.32 (m, 1H), 2.08 (m, 2H), 2.27 (m, 2H), 2.54 (d, J=7.5 Hz, 1H), 2.92(m, 1H), 4.45 (s, 1H); $^{13}C$ NMR ($CDCl_3$) δ216.6, 211.4, 87.7, 87.4, 57.6, 41.3, 39.2, 38.3, 25.1, 14.1, 13.4, 11.9; MS m/z 206 ($M^+$), 177, 149, 124; HRMS for $C_{12}H_{14}O_3$ calcd 206.0943, found 206.0941.

Compound 27

To a stirred solution of 7 (2.83 g, 13.7 mmol) and 2-propanol (500 ml) was added $K_2CO_3$ (8 g, 58.0 mmol) at 25° C. The mixture was stirred for 7 days, then partitioned between EtOAc and water. The organic extract was washed with saturated $NH_4Cl$ and dried over $MgSO_4$. Then the crude product was concentrated and chromatographed to give 1.88 g of 7 and 0.78 g of 27 (82.1%). 27 is a white solid: mp 183°–5° C.; IR (KBr) 3369, 2995, 1696, 1616, 1407, 1367, 1226 $cm^{-1}$; $^1H$ NMR ($CDCl_3$) δ1.24 (m, 1H), 1.38 (m, 1H), 1.68 (m, 1H), 1.88 (m, 1H), 2.00(s, 3H), 2.16(m, 2H), 2.46(m, 2H), 3.21(m, 1H), 4.06(d,J=2.7 Hz, 1H); $^{13}C$ NMR ($CDCl_3$) δ206.1, 204.8, 147.5, 128.0, 72.0, 42.2, 39.5, 32.1, 21.7, 19.4, 18.6, 11.7; MS m/z 206 ($M^+$), 177, 150, 147; HRMS for $C_{12}H_{14}O_3$ calcd 206.0943, found 206.0944.

Compound 28 p-Tolunesulfonic acid (12 mg, 0.063 mmol) was added to a stirred solution of 27 (107 mg, 0.519 mmol) and ethylene glycol (3.04 g, 49 mmol) in benzene (10 ml) at 25° C. which was then stirred for 24 h. The mixture was partitioned between EtOAc and saturated $NaHCO_3$. The combined organic layers were washed with saline, dried over $MgSO_4$ and concentrated to an oil which was chromatographed to give 5 mg of 27 and 118 mg of 28 (95.3%) as colorless oil: IR (KBr) 3469, 2952, 2892, 1757, 1690, 1616, 1374, 1159, 1085 $cm^{-1}$; $^1H$ NMR ($CDCl_3$) δ1.00 (m, 3H), 1.36 (m, 1H), 1.88 (d, J=2.7 Hz, 3H), 1.96 (m, 2H), 2.36 (m, 2H), 3.19 (t, J=3.9 Hz, 1H), 3.78 (t, J=3.9 Hz, 1H), 4.00 (m, 4H); $^{13}C$ NMR ($CDCl_3$) δ205.4, 148.3, 128.3, 108.9, 67.9, 65.6, 64.5, 41.9, 39.3, 26.8, 20.8, 12.8, 11.5, 6.22; MS m/z 250 ($M^+$), 221,193, 177; HRMS for $C_{14}H_{18}O_4$ calcd 250.1205, found 250.1201.

Compound 29

To a stirred solution of 28 (8.0 mg, 0.032 mmol) and pyridine (0.5 ml) was added TESCl (0.1 ml, 0.25 mmol) under $N_2$. The reaction mixture was stirred at 60° C. for 30 min and then concentrated to an oil. The crude product was purified by chromatography to give 13 mg of 29 (quantitative) as a colorless oil: IR (KBr) 2959, 2885, 1710, 1610, 1454, 1414, 1381, 1219 $cm^{-1}$; $^1H$ NMR ($CDCl_3$) δ0.62 (q, J=7.8 Hz, 6H), 0.94 (m, 11H), 1.28 (m, 1H), 1.83 (m, 1H), 1.87 (d, J=2.4 Hz, 3H), 2.35 (m, 2H), 3.13 (m, 2H), 3.75 (d, J=3.3 Hz, 1H), 4.01 (m, 4H); $^{13}C$ ($CDCl_3$) δ205.6, 148.8, 128.8, 109.5, 69.1, 65.3, 64.7, 43.3, 39.5, 27.4, 21.5, 12.9, 11.6, 6.8, 6.5, 4.8; MS m/z 364 ($M^+$), 336, 291, 219, 161; HRMS for $C_{20}H_{32}O_4Si$ calcd 364.2070, found 364.2070.

Compound 30

A solution of 29 (13 mg, 0.0357 mmol and phenylseleninic anhydride (13 mg, 0.0361 mmol) in chlorobenzene (0.5 ml) was stirred at 95° C. for 0.5 h under $N_2$. The solution was then concentrated and chromatographed to give 4.9 mg of 29 and 7.0 mg of 30 (78.2%) as colorless oil: IR (KBr) 2959, 2878, 1716, 1683, 1622, 1454, 1381, 1213 $cm^{-1}$; $^1H$ NMR ($CDCl_3$) δ0.54 (q, J=6.3 Hz, 6H), 0.89 (m, 10H), 1.27 (m, 2H), 1.57 (m, 1H), 1.93 (m, 3H), 3.79 (s, 1H), 4.00 (m, 4H), 6.30 (dd, J=2.4, 6 Hz, 1H), 7.28 (dd, J=2.1, 6 Hz, 1H); $^{13}C$ NMR ($CDCl_3$) δ195.9, 154.7, 146.9, 137.7, 127.5, 109.5, 69.2, 65.5, 64.6, 47.4, 28.0, 12.8, 11.1, 7.1, 6.7, 5.0; MS m/z 362 (M+), 333, 289, 187, 159, 87; HRMS for $C_{20}H_{30}O_4Si$ calcd 362.1913, found 362.1919.

Compound 34

To the solution of 30 (20 mg, 0.055 mmol and $CeCl_3.7H_2O$ (35 mg, 0.094 mmol) in MeOH (1 ml) was added $NaBH_4$ (excess). The mixture was stirred for 15 min at 25° C. and then more $NaBH_4$ was added. After 15 min of stirring the mixture was partitioned between $Et_2O$ and saturated $NH_4Cl$. The ether extract was dried over $MgSO_4$ and concentrated to give crude product 31 as pale yellow oil.

To the solution of the above crude product 31 in $CH_2Cl_2$ (1 ml) was added $Et_3N$ (20 ml, 0.143 mmol) and MsCl (20 ml, 0.258 mmol) respectively at 25° C. It was stirred for 5 min. Then the mixture was partitioned between $Et_2O$ and saturated $NaHCO_3$. The ether extract was washed by saline and dried over $MgSO_4$. After concentration, it was chromatographed to give 33 and 34 as yellow gum.

To the solution of the above compound 33 in acetone (2 ml) and water (1 ml) was added some p-TsOH at room temperature. The mixture was set aside for 5 min and partitioned between $Et_2O$ and saturated $NaHCO_3$. Then the ether extract was washed by saline and dried by $MgSO_4$. After concentration and chromatography, it was mixed with the above product 34 to give 10.5 mg of 34 as yellow gum: IR (KBr) 3456, 2912, 2885, 1730, 1636, 1441, 1367 cm$^{-1}$; $^1$H NMR (CDCl$_3$) δ0.75 (m, 1H), 1.10 (m, 2H), 1.24 (m, 1H), 1.88 (s, 3H), 2.34 (d, J=6.9 Hz, 1H), 3.95 (m, 2H), 4.06 (m, 2H), 4.68 (d, J=5.7 Hz, 1H), 6.34 (m, 1H), 6.42 (m, 2H); $^{13}$C NMR (CDCl$_3$) d 152.0, 139.8, 134.6, 130.5, 125.3, 117.9, 111.9, 71.3, 67.0, 66.1, 31.5, 16.4, 9.5, 6.6; MS m/z 232 (M+), 215, 189, 160, 145; HRMS for $C_{14}H_{16}O_3$ calcd 232.1099, found 232.1093.

Compound 35

A solution of 34 (7.3 mg, 31 mmol) and pyridinium dichromate (26 mg, 69 mmol) in $CH_2Cl_2$ (1 ml) was stirred for 1 h at 25° C. The mixture was diluted by $Et_2O$ and then filtered. The concentrated crude product was chromatographed to give 5.2 mg of 35 (71.9%) as yellow crystal: mp 138°–140° C.; IR (KBr) 2959, 2892, 1683, 1616, 1549, 1441, 1360 cm$^{-1}$; 1H NMR (CDCl$_3$) δ1.14 (m, 2H), 1.35 (m, 2H), 2.06 (s, 3H), 4.02 (m, 2H), 4.16 (m, 2H), 6.63 (dd, J=2.4, 4.8 Hz, 1H), 6.76 (d, J=4.8 Hz, 1H), 7.39 (s, 1H); $^{13}$C NMR (CDCl$_3$) δ187.6, 159.6, 140.3, 135.4, 131.0, 127.9, 124.8, 106.2, 66.0, 33.4, 16.9, 12.9; MS m/z 230 (M+), 202, 158; HRMS for $C_{14}H_{14}O_3$ calcd 230.0942, found 230.0948; UV γ$_{max}$(methanol) 230 nm (e 6543), 330 (e 3484).

Example II—Synthesis of Compound 42

Compound 36

To a solution of 27 (Example II) (37 mg, 0.18 mmol) in pyridine (3 ml) was added TESCl (0.25 ml, 0.624 mmol). The mixture was stirred at 60° C. for 0.5 h under $N_2$. After concentration and chromatography, it gave 50 mg of 36 (87%) as colorless oil: IR (KBr) 2952, 2872, 1703, 1622, 1461, 1414, 1226 cm$^{-1}$; $^1$H NMR (CDCl$_3$) δ0.58 (q, J=7.8 Hz, 6H), 0.97 (m, 10H), 1.25 (m, 2H), 1.58 (m, 1H), 1.85 (m, 2H), 1.98 (s, 3H), 2.42 (m, 2H), 3.09 (b, 1H), 4.01 (d, J=3 Hz, 1H); $^{13}$C NMR (CDCl$_3$) δ206.0, 205.0, 147.0, 128.6, 72.6, 43.0, 39.6, 32.1, 21.4, 19.6, 18.0, 11.5, 6.5, 4.5; MS m/z 320 (M+), 291, 259, HRMS for $C_{18}H_{28}O_3Si$ calcd 320.1808, found 320.1803.

Compound 37

The solution of 36 (278 mg, 0.869 mmol) and phenylseleninic anhydride (320 mg, 0.889 mmol) in chlorobenzene (2.5 ml) was stirred at 95° C. for 0.5 h under $N_2$. The mixture was then concentrated and chromatographed to give 58.7 mg of 36 and 131.2 mg of 37 (60.2%) as colorless gum: IR (KBr) 2952, 2878, 1730, 1690, 1636, 1454, 1240 cm$^{-1}$; $^1$H NMR (CDCl$_3$) δ0.52 (q, J=7.8 Hz, 6H), 0.85 (t, J=7.8 Hz, 9H), 1.20 (m, 1H), 1.36 (m, 1H), 1.69 (m, 1H), 1.82 (m, 1H), 2.06 (s, 3H), 3.58 (s, 1H), 4.26 (d, J=2.4 Hz, 1H), 6.45 (dd, J=2.1, 6 Hz, 1H), 7.33 (dd, J=2.1, 6 Hz, 1H); $^{13}$C NMR (CDCl$_3$) δ205.9, 195.3, 153.2, 144.3, 139.4, 127.7, 72.1, 47.3, 32.4, 20.1, 19.7, 11.4, 6.4, 4.4; MS m/z 318 (M+), 289, 261; HRMS for $C_{18}H_{26}O_3Si$ calcd 318.1651, found 318.1658.

Compound 40

To a solution of 37 (9.5 mg, 0.0299 mmol), $CeCl_3.7H_2O$ (58.5 mg, 0.157 mmol) in MeOH (0.3 ml) was added $NaBH_4$ (excess) at 25° C. It was stirred for 30 min. Then the mixture was partitioned between $Et_2O$ and saturated $NH_4Cl$. The ether extract was dried by $MgSO_4$ and concentrated to give crude product 38 as pale yellow oil.

To the solution of above 38 in $CH_2Cl_2$ (0.2 ml) was added $Et_3N$ (5 ml, 0.036 mmol) and MsCl (5 ml, 0.965 mmol) at 25° C. The mixture was stirred for 5 min and then separated between $Et_2O$ and saturated $NaHCO_3$. Then the ether extract was washed by saline and dried by $MgSO_4$. After concentration, it was chromatographed to give 8.2 mg of 40 (90.3%) as yellow gum: IR (KBr) 3557, 3449, 2946, 2878, 1716, 1643, 1461, 1112 cm$^{-1}$; $^1$H NMR (CDCl$_3$) δ0.66 (q, J=7.8 Hz, 6H), 0.87 (m, 2H), 0.98 (t, J=7.8 Hz, 9H), 1.26 (m, 2H), 1.86 (s, 3H), 2.55 (d, J=3.9 Hz, 1H), 3.24 (s, 1H), 4.94 (d, J=2.1 Hz, 1H), 6.35 (m, 2H), 6.46 (m, 1H); $^{13}$C NMR (CDCl$_3$s) δ148.9, 140.0, 130.4, 117.8, 117.5, 77.0, 68.6, 61.9, 16.1,11.6, 7.8, 6.8, 5.0; MS m/z 304 (M+), 287, 275; HRMS for $C_{18}H_{28}O_2Si$ calcd 304.1859, found 304.1860.

Compound 41

A solution of 40 (1.2 mg, 3.95 mmol) and Dess-Martin reagent (2.2 mg, 5.19 mmol) in $CH_2Cl_2$ (0.2 ml) was stirred for 30 min at 25° C. The mixture was separated between $Et_2O$ and 10% $Na_2SO_3$. Then the ether extract was washed by saline and dried by $MgSO_4$. After concentration, it was chromatographed to give 1.1 mg of 41 (92.3%) as yellow gum: IR (KBr) 2952, 2872, 1690, 1610, 1549, 1354, 1132 cm$^{-1}$; $^1$H NMR (CDCl$_3$) δ0.71 (q, J=7.8 Hz, 6H), 0.85 (m, 1H), 0.97 (t, J=7.8 Hz, 9H), 1.21 (m, 2H), 1.45 (m, 1H), 2.08 (s, 3H), 4.50 (s, 1H), 6.66 (dd, J=2.4, 4.8 Hz, 1H), 6.72 (d, J=5.1 Hz, 1H), 7.25 (s, 1H); $^{13}$C NMR (CDCl$_3$) δ193.3, 161.2, 140.7, 131.8, 131.2, 128.3, 122.8, 32.9, 17.1, 12.5, 10.3, 6.9, 5.2; MS m/z 302 (M+), 273, 245; HRMS for $C_{18}H_{26}O_2Si$ calcd 302.1702, found 302.1710; UV γ$_{max}$227 nm (e 15612), 323 nm (e 10720).

Compound 42

To a solution of 41 (9.0 mg, 0.0298 mmol) in acetone (0.8 ml) and $H_2O$ (0.4 ml) was added some p-TsOH. The mixture was stirred for 30 min. Then it was partitioned between $Et_2O$ and saturated $NaHCO_3$. The ether extract was washed by saline and dried by $MgSO_4$. After concentration, it was chromatographed to give quantitative 42 as yellow gum: IR (KBr) 3449, 3013, 2925, 1663, 1609, 1441, 1367, 1260 cm$^{-1}$; $^1$H NMR (CDCl$_3$) δ0.81 (m, 1H), 1.25 (m, 1H), 1.36 (m, 1H), 1.44 (m, 1H), 2.12 (s, 3H), 3.82 (d, J=2.4 Hz, 1H), 4.55 (d, J=2.1 Hz, 1H), 6.70 (dd, J=2.7, 5.1 Hz, 1H), 6.81 (t, 1H), 7.32 (s, 1H); $^{13}$C NMR (CDCl$_3$) δ194.2, 162.2, 140.9, 132.7, 131.4, 126.5, 124.1, 74.6, 32.8, 17.0, 12.7, 10.3; MS m/z 188 (M+), 160, 145; HRMS for $C_{12}H_{12}O_2$ calcd 188.0837, found 188.0840; UV γ$_{max}$(methanol) 227 nm (e 13626), 323 nm (e 7474).

All publications, patents and patent documents are incorporated by reference herein, as though individually incorporated by reference. The invention has been described with reference to various specific and preferred embodiments .and techniques. However, it should be understood that many variations and modifications may be made while remaining within the spirit and scope of the invention.

I claim:

1. A method of synthesizing a compound of formula (V):

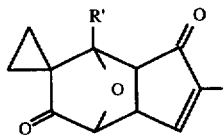

wherein R' is $(C_1-C_4)$alkyl; comprising the steps of coupling a cyclopentenone of formula (II):

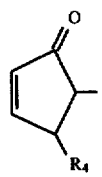

wherein $R_4$ is —O—$C(R_9)_2O(R_9)$, wherein $R_9$ is $(C_1-C_4)$ alkyl;

with a cyclic carbonyl ylide dipole of formula (III):

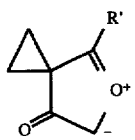

to form a compound of formula (IV):

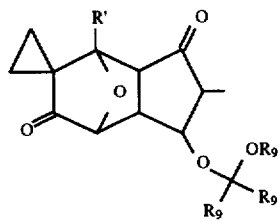

and treating compound (IV) with base to form a ketone of formula (V).

2. The method of claim 1 further comprising the steps of dihydroxylating the ketone to yield a compound of formula (VI):

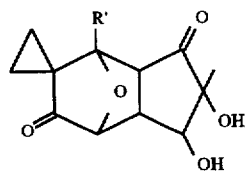

and treating the compound of formula (VI) with a removable 1,2-diol protecting reagent to yield an intermediate of formula (VII):

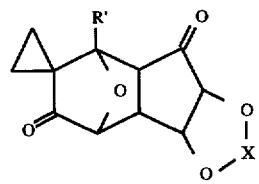

wherein X is a removable 1,2-diol protecting group.

3. The method of claim 2 further comprising the steps of treating compound of formula (VII) with RMgCl, where R is $(C_1-C_4)$alkyl, to yield a Grignard product of formula VIII:

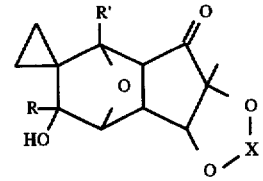

and cleaving the oxybridge to yield a diol of formula (IX):

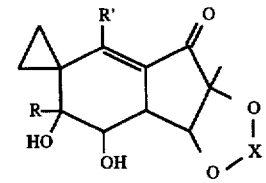

4. The method of claim 3 further comprising the step of removing the removable diol protecting group to yield a tetraol of formula (X):

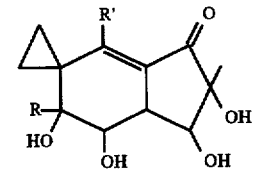

5. The method of claim 4 further comprising the steps of converting the tetraol to an orthoester of formula (XI):

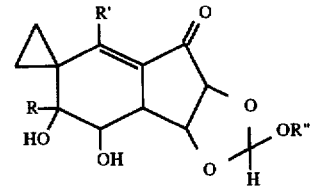

wherein R" is $(C_1-C_3)$alkyl; and eliminating the cis hydroxyls to yield a dienone of formula (XII):

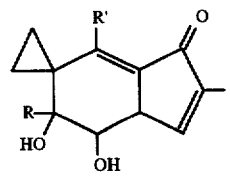

6. The method of claim 5 further comprising the steps of reducing the compound of formula (XII) to convert the ketone to an alcohol, under conditions which dehydrate the resulting alcohol to yield a fulvene of formula (XIII):
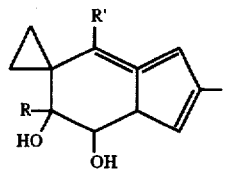
(XIII)
7. The method of claim 6 further comprising the step of oxidizing the fulvene of formula (XIII) to yield a compound of formula (I):
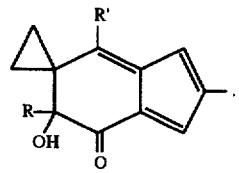
(I)
8. The method of claim 7 wherein $R_9$ is $CH_3$.
9. The method of claim 7 wherein R' is methyl.
10. The method of claim 7 wherein R is methyl.
* * * * *